United States Patent
Bogan, Jr. et al.

(10) Patent No.: US 9,701,610 B2
(45) Date of Patent: Jul. 11, 2017

(54) AMMONIUM BISULFATE CATALYZED DEHYDRATION OF BETA-HYDROXY ACIDS

(71) Applicants: Dow Global Technologies LLC, Midland, MI (US); Rohm and Haas Company, Philadelphia, PA (US)

(72) Inventors: Leonard E. Bogan, Jr., Midland, MI (US); Mark A. Silvano, Upper Black Eddy, PA (US); Raymond P. Roach, Midland, MI (US); Sarah M. Hoyt, Greenwood, CO (US); Robert Tengler, Longmont, CO (US); David C. Decoster, Lyons, CO (US); Sanjib Biswas, Midland, MI (US); Muhunthan Sathiosatham, Chalfont, PA (US); Sarah L. Hruby, North Wales, PA (US); Andrew M. Lemonds, Schwenksville, PA (US)

(73) Assignees: Dow Global Technologies LLC, Midland, MI (US); Rohm and Haas Company, Philadelphia, PA (US)

(*) Notice: Subject to any disclaimer, the term of this patent is extended or adjusted under 35 U.S.C. 154(b) by 0 days.

(21) Appl. No.: 15/028,109

(22) PCT Filed: Oct. 14, 2014

(86) PCT No.: PCT/US2014/060395
§ 371 (c)(1),
(2) Date: Apr. 8, 2016

(87) PCT Pub. No.: WO2015/057644
PCT Pub. Date: Apr. 23, 2015

(65) Prior Publication Data
US 2016/0244395 A1   Aug. 25, 2016

Related U.S. Application Data

(60) Provisional application No. 61/891,970, filed on Oct. 17, 2013.

(51) Int. Cl.
C07C 51/377 (2006.01)
B01J 27/24 (2006.01)
C07C 57/04 (2006.01)

(52) U.S. Cl.
CPC ............. *C07C 51/377* (2013.01); *B01J 27/24* (2013.01)

(58) Field of Classification Search
CPC .............................. C07C 51/377; B01J 27/24
(Continued)

(56) References Cited

U.S. PATENT DOCUMENTS 2,342,663 A    2/1944   Haddock
2,469,701 A    5/1949   Redmon
(Continued)

FOREIGN PATENT DOCUMENTS

WO    2011/038364 A1    3/2011
WO    2011/063363 A2    5/2011
(Continued)

OTHER PUBLICATIONS

Mao ("Synthesis and properties of poly(beta-acryloxypropionic acid) hydrogels" Polymer, vol. 36, No. 23, p. 4509-4513).*

*Primary Examiner* — Jafar Parsa
*Assistant Examiner* — Amy C Bonaparte
(74) *Attorney, Agent, or Firm* — Husch Blackwell LLP

(57) ABSTRACT

Hydroxycarboxylic acids, e.g., 3-hydroxypropionic acid, and/or their ammonium salts are dehydrated to their corresponding unsaturated carboxylic acids, e.g., acrylic acid, by a process that uses a catalyst comprising ammonium bisulfate. The use of ammonium bisulfate reduces or eliminates the problems associated with processes that use sulfuric acid as a dehydrating catalyst, e.g, excess sulfuric acid consumption and/or recovery.

12 Claims, 2 Drawing Sheets

(58) Field of Classification Search
USPC .......................................................... 562/599
See application file for complete search history.

(56) References Cited

U.S. PATENT DOCUMENTS

| | | |
|---|---|---|
| 3,911,092 A | 10/1975 | Bretherick |
| 3,929,977 A | 12/1975 | Brennan |
| 5,041,614 A | 8/1991 | Aslam et al. |
| 5,470,928 A | 11/1995 | Harwood et al. |
| 5,510,307 A | 4/1996 | Narayanan et al. |
| 6,709,919 B2 | 3/2004 | Tu |
| 7,678,869 B2 | 3/2010 | Matyjaszewski et al. |
| 7,687,661 B2 | 3/2010 | Lilga et al. |
| 7,943,362 B2 | 5/2011 | Frost |
| 8,198,481 B2 | 6/2012 | Kuppinger et al. |
| 2004/0210087 A1 | 10/2004 | Meng et al. |
| 2005/0221457 A1 | 10/2005 | Tsobanakis et al. |
| 2005/0222458 A1 | 10/2005 | Craciun et al. |
| 2007/0219390 A1* | 9/2007 | Zacher .................. C07C 51/377 560/205 |
| 2009/0062580 A1 | 3/2009 | Takai et al. |
| 2009/0298144 A1 | 12/2009 | Tsobanakis et al. |
| 2010/0113822 A1 | 5/2010 | Craciun et al. |
| 2011/0125118 A1 | 5/2011 | Lynch |
| 2011/0183391 A1 | 7/2011 | Frost |
| 2013/0345470 A1 | 12/2013 | Tengler et al. |

FOREIGN PATENT DOCUMENTS

| | | |
|---|---|---|
| WO | 2011/094457 A1 | 8/2011 |
| WO | 2013/192453 A1 | 12/2013 |

\* cited by examiner

Dehydration of A3HP and 3HP to Acrylic Acid Catalyzed by Recycled Sulfuric Acid

Dehydration of A3HP and 3HP to Acrylic Acid

Catalyzed by Recycled Ammonium Bisulfate

AMMONIUM BISULFATE CATALYZED DEHYDRATION OF BETA-HYDROXY ACIDS

BACKGROUND OF THE INVENTION

The invention relates to a process for preparing a carboxylic acid.

The beta-hydroxy acid, 3-hydroxypropionic acid (3HP) can be dehydrated to its corresponding unsaturated acid, acrylic acid (AA), under acidic conditions at elevated temperatures, generating water as a by-product. In the preparation of 3HP by fermentation of sugar(s), the necessity of operating the fermentation at or near neutral pH leads to formation of a 3HP salt, most commonly the ammonium salt (A3HP) as an aqueous solution. Gaseous or aqueous ammonia is used as a base titrant throughout the fermentation process to form A3HP, and the A3HP is converted to its free-acid form, namely 3HP, before it is converted to acrylic acid in a dehydration reaction. Conversion of A3HP to 3HP can be accomplished by various methods including: (A) mineral acid acidification, e.g., with sulfuric acid ($H_2SO_4$), or phosphoric acid ($H_3PO_4$); (B) same as (A) followed by stripping or evaporation of water and some volatile contaminants and their subsequent collection as a condensate (the 3HP remains in the liquid phase of the process); (C) solvent-based or solventless thermal salt splitting; (D) alkylamine assisted solvent extraction followed by back-extraction of the free-acid into water; and (E) the use of an electrolytic membrane device.

Subsequently, the 3HP free-acid produced in any of the above schemes may be dehydrated to acrylic acid by a strong mineral acid catalyst, such as concentrated sulfuric acid. Both heterogeneous solid-acid catalysts and homogeneous mineral acid catalysts have been described in the patent and open literature. In all of these schemes, the presence of residual ammonium ion ($(NH_4)^+$) is possible. Scheme (A) represents the extreme case where all of the ammonium ion remains and is present as ammonium sulfate (($NH_4)SO_4$) or ammonium bisulfate (($NH_4)HSO_4$). Lesser amounts of ammonium ion are expected to accompany the free-acid in the other schemes. When the free-acid-containing effluent of any of the above schemes is fed to concentrated sulfuric acid, 3HP is dehydrated to acrylic acid that can be removed by distillation, while any residual ammonium ion is converted to ammonium bisulfate in the liquid phase. The steady state sulfate salt composition of the dehydration reactor effluent is established by the mole ratio of sulfuric acid to ammonium ion. The salt composition can vary from predominantly ammonium sulfate (AS) at lower mole ratios (e.g., less than (<) 0.5), AS and ammonium bisulfate (ABS) mixtures at intermediate mole ratios (e.g. 0.7), and mixtures of ABS with excess sulfuric acid at mole ratios greater than (>) 1.0.

When an excess of sulfuric acid is used as the dehydration catalyst for the dehydration of hydroxycarboxylic acids to produce carboxylic acids, disposal of the reactor bottoms is difficult due to the corrosive nature of the stream. In one commercially practiced process, an acid recovery combustion process is used to convert sulfates into sulfuric acid and recycle the acid back to the dehydration reactor. The ammonia in the bottoms stream of the process, however, is not recovered. A sulfuric acid recovery unit employs a hazardous process, requires significant capital investment, and has significant environmental, health, and safety concerns.

Alternatively, the ammonia can be recovered at the cost of losing the sulfuric acid. For example, the gypsum process, in which gypsum ($CaSO_4$) is produced from the reaction of calcium oxide (CaO, lime) with ammonium sulfate, provides such an alternative. The recovered ammonia is then fed back to the fermenters. The gypsum, however, has too high of an organics content to be sold, and there are limited landfill options because as gypsum breaks down it generates hydrogen sulfide ($H_2S$), which is toxic and causes corrosion of the turbines used to generate energy from landfill gases.

In view of the disadvantages of the existing processes, an improved process for the dehydration of hydroxycarboxylic acids and their ammonium salts to carboxylic acids is desirable. In addition, an alternative to the conventional sulfuric acid catalyst system from which both ammonia and the dehydration catalyst can be recovered and that provides a simpler and milder catalyst regeneration process is also desireable.

SUMMARY OF THE INVENTION

In one embodiment the invention is a process comprising the steps of:
(A) Contacting in a reaction zone and under dehydration reaction conditions a beta-hydroxy carboxylic acid and/or its ammonium salt with a catalytic amount of a catalyst comprising ammonium bisulfate (ABS) to form a dehydrated carboxylic acid, water and ammonium sulfate (AS),
(B) Removing a vapor stream comprising the dehydrated carboxylic acid and water from the reaction zone,
(C) Removing a liquid stream comprising AS from the reaction zone,
(D) Forwarding the vapor stream to a purification zone in which the dehydrated carboxylic acid is separated from water,
(E) Forwarding the liquid stream comprising AS to a thermal conversion zone in which the AS is converted to ABS and ammonia,
(F) Optionally, recycling the ABS from step (E) to step (A),
(G) Optionally, recovering ammonia from the thermal conversion zone, and
(H) Optionally, removing a purge stream comprising ABS and/or AS prior to or at or near the beginning of the thermal conversion zone.

In one embodiment the process is continuous. In one embodiment the beta-hydroxy carboxylic acid is 3HP and it is converted to AA. The process of this invention reduces or eliminates the problems associated with excess sulfuric acid consumption and recovery.

DETAILED DESCRIPTION OF THE INVENTION

Definitions

Figure 1:
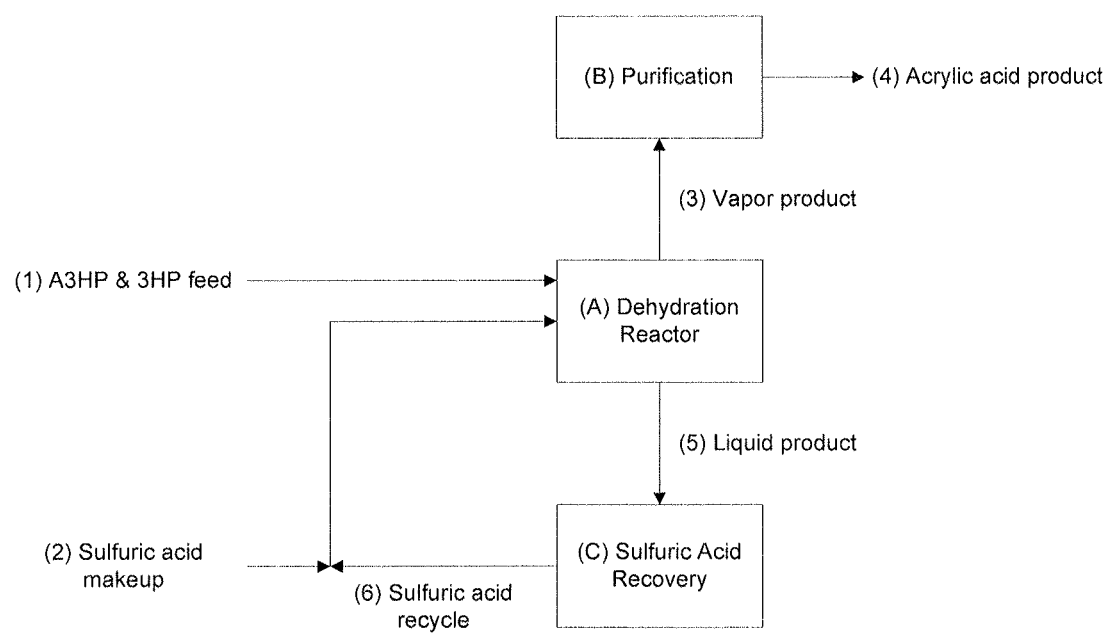
FIG. 1 is schematic flow chart describing the dehydration of A3HP and 3HP to AA by recycled sulfuric acid catalysis.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

"3HP" means 3-hydroxypropionic acid (CAS number 503-66-2).

"A3HP" means the ammonium salt of 3HP.

3HP and A3HP are collectively referred to as HP.

"Biologically produced 3HP" and like terms mean that the primary source of the 3HP is plant or microbial, typically produced in a fermentor. "Derived from biologically produced 3HP" and like terms mean that the a derivative product, e.g., A3HP, is made, directly or indirectly, from biologically produced 3HP.

"AA" means acrylic acid (CAS number 79-10-7).

"SA" means sulfuric acid.

The term "fermentation broth" refers to a mixture derived from a fermentation process. A fermentation broth may be a mixture obtained from a microbial fermentation process without any purification or separation. Alternatively, a fermentation broth may be a mixture obtained from a microbial fermentation procedure after purification or separation. A fermentation broth may be clarified. A fermentation broth may contain whole cells or may be substantially free of whole cells. Additionally, a fermentation broth may be treated, for example, with a lysing agent to release a desired compound or compounds from cells.

"Dehydration reaction conditions" and like terms mean the temperature, pressure and other conditions at which a beta-hydoxy carboxylic acid and/or its salt is converted to a dehydrated carboxylic acid and water. For the conversion of 3HP and/or A3HP to AA, the temperature is typically of 100° C. to 250° C., more typically of 130° C. to 200° C. and even more typically of 150° C. to 170° C., and the pressure is typically from 26.6 kiloPascals (KPa) to atmospheric (101.3 KPa).

Starting Materials

The process of the invention employs 3HP and/or A3HP, a dehydration catalyst, and water.

In some embodiments of the invention, the HP is provided in an aqueous solution produced by a fermentation process. A crude fermentation broth may be clarified (e.g., by filtration, precipitation, or centrifugation) to obtain a clarified fermentation broth prior to dehydration. In some embodiments, the pH of the fermentation broth is in a range of about 4.5 to about 8.0, about 5.0 to about 7.8, or about 5.5 to about 7.6. In those embodiments in which ammonia is used as a titrant during fermentation, at least a portion of the HP exists as a salt, and preferably a substantial amount of the HP is in an ammonium salt form. Utilizing the ammonium salt provides multiple cost advantages, including allowing for recycling of ammonia to fermentation, and avoiding the need to fabricate equipment with costly acid-resistant metals. In some cases, the HP may exist as at least about 60%, at least about 70%, at least about 80%, at least about 90%, or at least about 95% as the ammonium salt.

In some cases, the aqueous HP solution is a fermentation broth. In some cases, the aqueous solution of HP is derived from a fermentation broth. In some cases, the HP has been produced by a microorganism. In some cases, the HP has been chemically synthesized. In some cases, the HP comprises at least about 90% by weight of 3HP that is biologically produced or derived from biologically produced 3HP. In some cases, the HP comprises at least about 95%, or at least about 98% by weight of a biologically produced HP.

In some cases, a composition described herein has a 14C concentration of at least 1 part per trillion carbon, or about 1.2 parts per trillion carbon. In some cases, the clarified HP solution is concentrated to generate a concentrated HP solution.

In some cases at least a portion of the HP in the aqueous solution exists as an ammonium salt. In some cases, a substantial portion of the HP in the aqueous solution exists as an ammonium salt. In some cases, at least about 60% of the HP in the aqueous solution exists as an ammonium salt. In some cases, at least about 70% of the HP in the aqueous solution exists as an ammonium salt. In some cases, at least about 80% of the HP in the aqueous solution exists as ammonium salt in some cases, at least about 90% of the HP in the aqueous solution exists as an ammonium salt. In some cases, some of the 3HP may be present as a dimer (coupled through an ester linkage) or trimer of HP.

Catalyst

The preferred dehydration catalyst is ammonium bisulfate (ABS). It can be supplied to the process as ABS or preferably it can be formed in situ in the reaction system via the reaction of sulfuric acid (SA) with ammonia or an ammonium salt, such as A3HP. ABS and SA are well known and widely commercially available. The catalyst is employed in a catalytic amount, i.e any amount that is sufficient to catalyze the reaction or in other words, accelerate the dehydration of the beta-hydoxy carboxylic acid. The relative amounts of SA, ABS, and ammonium sulfate (AS) present in the reactor depend on the amounts of SA and ammonia (or ammonium ion) added. If the ratio of SA:ammonia is greater than 1.0, then a mixture of SA and ABS will be present. If the ratio of SA:ammonia is less than 1.0, then a mixture of ABS and AS will be present. Advantageously, the ABS is molten or in solution in the reactor.

The initial catalyst charge to the reactor may consist of ABS or sulfuric acid. If sulfuric acid is used for the charge, then preferably no bottoms will be drawn off until the concentration of A3HP reaches the desired operating acid/ammonium ion ratio. Supplemental sulfuric acid will be necessary to maintain the preferred steady-state ammonium bisulfate/ammonium sulfate composition ratio when a purge stream is removed from the recycled ABS stream. The size of the purge stream, and correspondingly, the size of the make-up sulfuric acid stream will depend on the amount of impurities in the A3HP/3HP feed, which may include inorganic salts and fermentation impurities such as proteins, amino acids, sugars, and other carboxylic acids or salts.

In one embodiment water is employed as a mass transfer aid and/or solvent. In one embodiment neither water nor any other mass transfer aid and/or solvent is employed since 3HP is liquid under ambient conditions, e.g., room temperature (20-23° C.) and atmospheric pressure, and liquid 3HP can solubilize A3HP. The amount of water in the reactor at steady state reaction conditions is sufficient to facilitate the transfer of acrylic acid from the liquid phase to the vapor phase. The amount of water in the vapor phase is a function of the amount of water in the feed to the reactor. Typically the amount of water in the feed is from 3 to 90 weight percent (wt %), and the amount of water in the vapor phase is from 0 or greater than 0 to 10 wt %, or from 0 or greater than 0 to 5 wt %. In one embodiment of the invention, additional water is added to maintain a desired level of water in the reactor. In one embodiment water is used during start-up of a reactor in which ammonium bisulfate is used as a catalyst without sulfuric acid present.

Process

In the present invention ABS is used as a catalyst for the dehydration of a beta-hydroxy acid, 3HP and/or A3HP into AA, an unsaturated carboxylic acid. The 3HP and/or A3HP is produced by a fermentation process, which may be followed by clarification and/or concentration of the fermentation broth. The dehydration reactor preferably is a continuous, stirred reactor, operated at a temperature from the melting point of ABS, which is 147° C., up to 250° C. The reactor may be operated at atmospheric pressure or under vacuum. The AA that is produced exits the reactor in the vapor phase, along with water (which enters in the feed or is produced in the reactor) and possibly other impurities. The ammonium ion that is present in the A3HP that is fed to the reactor reacts in the liquid phase with ABS to form AS. The liquid stream leaving the dehydration reactor contains AS and/or ABS, along with non-volatile impurities in the feed stream, which may include inorganic salts, residual biomass, and other impurities.

The ABS catalyst is regenerated from AS in a thermal conversion process, which is known to those skilled in the art. The regenerated ABS produced by this process is recycled to the dehydration reactor. The ABS regeneration process also recovers ammonia, which can then be recycled to the fermentors used to produce the 3HP and/or A3HP. A purge stream may be necessary to remove impurities such as inorganic salts, which may otherwise accumulate in the recycle loop. If a purge is employed, a sulfuric acid make-up stream may be required to maintain the desired reactor ABS/AS composition.

Purification of the AA downstream of the dehydration reactor, using operations such as distillation and/or crystallization may produce a byproduct or residual stream containing AA and acryloxypropionic acid (AOPA, a dimer of AA). This stream may be recycled to the dehydration reactor to convert AOPA back to AA and to recover the AA present in this stream. The recycle of this stream does not require a change in the operating conditions of the dehydration reactor.

FIG. 1 illustrates the dehydration of A3HP and 3HP to acrylic acid catalyzed by recycled sulfuric acid. Stream 1 containing A3HP and 3HP is fed to dehydration reactor A. Vapor stream 3 leaving dehydration reactor A is fed to purification process B which may include distillation, crystallization, or a combination of distillation and crystallization to produce final acrylic acid product 4. Liquid stream 5 leaving dehydration reactor A is fed to sulfuric acid recovery process C. Recovered sulfuric acid 6 is returned to dehydration reactor A. Smaller sulfuric acid stream 2 is fed to the reactor to make up for losses of sulfuric acid from sulfuric acid recovery process C. The ammonia entering the reaction system as A3HP is not recovered.

Figure 2:
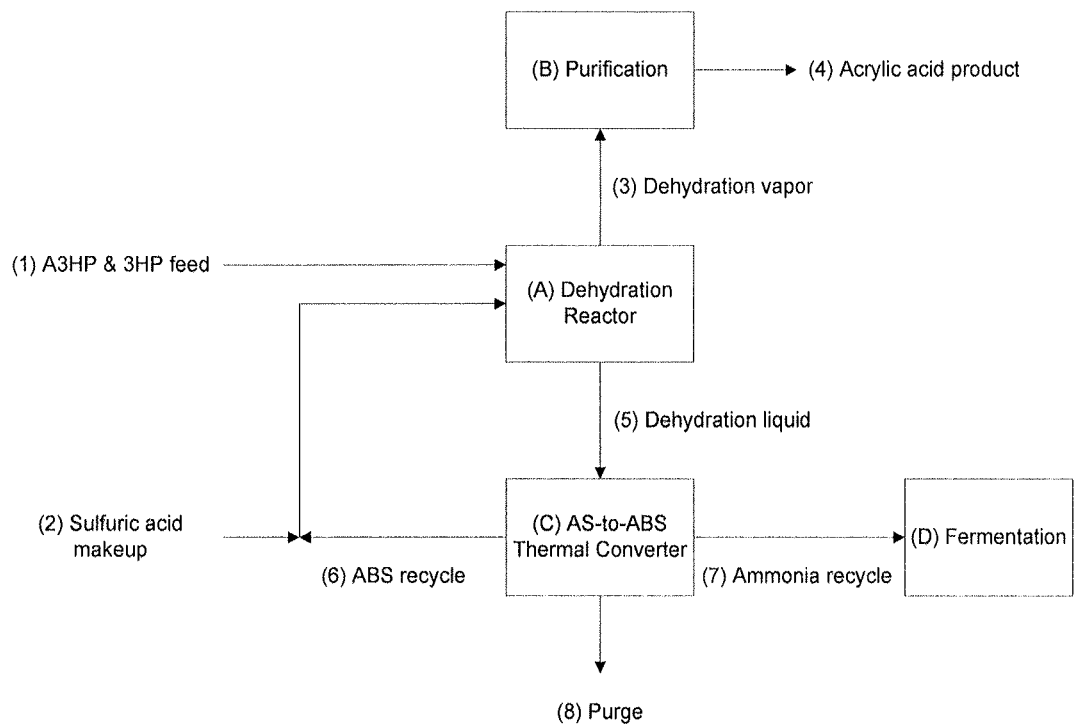
FIG. 2 is a schematic flow chart describing the dehydration of A3HP and 3HP to AA by recycled ABS.

FIG. 2 illustrates the dehydration of A3HP and 3HP to acrylic acid by recycled ABS. The stream containing A3HP and 3HP (1) is fed to dehydration reactor A. The vapor stream 3 leaving the dehydration reactor is fed to purification process B which may include distillation, crystallization, or a combination of distillation and crystallization to produce final acrylic acid product 4. Liquid stream 5 leaving dehydration reactor A is fed to a thermal conversion zone in which the AS is converted to ABS and ammonia C. Recovered ABS 6 is returned to dehydration reactor A. Smaller sulfuric acid make-up stream 2 is fed to maintain the preferred steady-state ammonium bisulfate/ammonium sulfate composition ratio when a purge stream 8 is removed from the recycled ABS stream 6. The ammonia can then be recycled 7 to the fermentors D used to produce the 3HP and/or A3HP.

Fermentation Broth

The fermentation broth used herein contains HP. A variety of microbial systems for producing 3-HP are described in the art such as in, for example, U.S. Pat. No. 6,852,517 and US 2011/0125118 and 2008/0199926. It is understood that these references and the following discussion provide examples to which the present invention can he applied. They are meant to be illustrative. As one of ordinary skill in the art will readily understand, the invention can be applied to a variety of plant and microbial systems which produce 3HP and related compounds.

The microbial systems may comprise a carbon source, one or more microorganisms, and suitable media and culture conditions. The fermentation may be carried out in a bioproduction reactor. After fermenting for a certain period of time, the crude cell broth obtained may be further processed to yield high purity 3HP or downstream products and in one embodiment, using the process of this invention.

The carbon source may be any carbon source suitable for the intended metabolic pathway. Suitable carbon sources may include, but are not limited to, monosaccharides such as glucose and fructose, oligosaccharides such as lactose or sucrose, polysaccharides such as starch or cellulose or mixtures thereof and impurified mixtures from renewable feedstocks such as cheese whey permeate, corn steep liquor, sugar beet molasses, and barley malt. Additionally, the carbon substrates may also be one-carbon substrates such as carbon dioxide, carbon monoxide, or methanol for which metabolic conversion into key biochemical intermediates has been demonstrated. In addition to one and two carbon substrates, methylotrophic organisms are also known to utilize a number of other carbon containing compounds such as methylamine, glucosamine and a variety of amino acids for metabolic activity.

The microorganism may have one or more natural, introduced, or enhanced 3-HP bio-production pathways. The microorganism may comprise an endogenous 3-HP production pathway. The endogenous 3-HP production pathway may be enhanced to increase 3-HP production. On the other hand, the microorganism may not comprise an endogenous 3-HP production pathway. In this case, the pathway can be introduced through, for example, genetic engineering. A microorganism may be selected from bacteria, cyanobacteria, filamentous fungi, and yeasts. Since 3-HP produced during fermentation may be toxic to the microorganism used in the process, the microorganism may further comprise modifications to increase tolerance to 3-HP.

Microorganisms may include, but are not limited to, any gram negative organisms, more particularly a member of the family Enterobacteriaceae, such as *E. coli, Oligotropha carboxidovorans*, or *Pseudomononas* sp.; any gram positive microorganism, for example *Bacillus subtilis, Lactobacillus* sp. or *Lactococcus* sp.; a yeast, for example *Saccharomyces cerevisiae, Pichia pastoris* or *Pichia stipitis*; and other groups or microbial species. More particularly, suitable microbial hosts for the bio-production of 3-HP generally include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula*, and *Saccharomyces*. Hosts that may be particularly of interest include: *Oligotropha* carboxidovorans (such as strain OM5), *Escherichia coli, Alcaligenes eutrophus (Cupriavidus* necator), *Bacillus licheniformis, Paenibacillus macerans, Rhodococcus erythropolis, Pseudomonas putida, Lactobacillus plantarum, Enterococcus faecium, Enterococcus gallinarium, Enterococcus faecalis, Bacillus subtilis*, and *Saccharomyces cerevisiae*.

There may be a variety of pathways and/or mechanisms to increase 3-HP production, for example, reducing the activity of fatty acid synthase and/or enhancing the activity of malonyl-CoA reductase. The modulation of the pathways can be achieved by a variety of methods described in the art, such as those provided in WO/2011/038364, WO/2011/063363, and WO/2011/094457. Particular enzymes and metabolic pathways are taught in U.S. Pat. No. 7,943,362 and US Publication No. US2011/0183391. In addition, one or more additives may be added to the cell culture to modulate fatty acid synthase or malonyl-CoA reductase to increase the production of 3-HP.

In addition to an appropriate carbon source, bio-production media may contain suitable minerals, salts, cofactors, buffers, and other components, known to those skilled in the art, suitable for the growth of the cultures and promotion of the enzymatic pathways necessary for the production of 3-HP or other products.

Typically cells are grown at a temperature in the range of about 25° C. to about 40° C. (or up to 70° C. for thermophilic microorganisms) in an appropriate medium comprising water. Suitable growth media include common commercially prepared media such as Luria Bertani (LB) broth, M9 minimal media, Sabouraud Dextrose (SO) broth, yeast medium (YM) broth, yeast synthetic minimal media (Ymin), and minimal media such as M9 minimal media. Other defined or synthetic growth media may also be used, and the appropriate medium for growth of the particular microorganism will be known by one skilled in the art of microbiology or bio-production science. In various embodiments a minimal media may be developed and used that does not comprise, or that has a low level of certain components, for example less than 10, 5, 2 or 1 g/L of a complex nitrogen source including but not limited to yeast extract, peptone, tryptone, soy flour, corn steep liquor, or casein. These minimal media may also be supplemented with vitamin mixtures including biotin, vitamin B12 and derivatives of vitamin B12, thiamin, pantothenate and other vitamins. Minimal medias may also comprise simple inorganic nutrient sources containing less than 40, 17, or 2.5 mM phosphate, less than 25 or 4 mM sulfate, and/or less than 130 or 50 mM total nitrogen all measured as of the start of the fermentation.

Bio-production media may contain suitable carbon substrates for the intended metabolic pathways. As described elsewhere in this disclosure, suitable carbon substrates may include carbon monoxide, carbon dioxide, various monomeric and oligomeric sugars, amines, and amino acids.

Suitable pH ranges for bio-production may be between pH 3.0 to pH 10.0, where pH 6.0 to pH 8.0 is a typical pH range for the initial condition. However, the actual culture conditions for a particular embodiment are not meant to be limited by these pH ranges.

Bio-production may be performed under aerobic, microaerobic, or anaerobic conditions, with or without agitation and with or without external heating or cooling. The amount of 3-HP or other product(s) produced in a bio-production medium generally can be determined using a number of methods known in the art, for example, high performance liquid chromatography (HPLC), gas chromatography (GC), or GC/mass spectroscopy (MS).

Any suitable microorganism, including the microorganisms described in this disclosure, may be introduced into an industrial bio-production system where the microorganisms convert a carbon source into 3HP in a commercially viable operation. The bio-production system includes the introduction of such a microorganism into a bioreactor vessel, with a carbon source substrate and bio-production media suitable for growing the microorganism, and maintaining the bio-production system within a suitable temperature range (and dissolved oxygen concentration range if the reaction is aerobic or microaerobic) for a suitable time to obtain a desired conversion of a portion of the substrate molecules to 3HP. The fermentation process may be monitored by measuring the concentration of 3HP in crude fermentation broth. Industrial bio-production systems and their operation are well-known to those skilled in the arts of chemical engineering and bioprocess engineering.

The operation of cultures and populations of microorganisms to achieve aerobic, microaerobic and anaerobic conditions are known in the art, and dissolved oxygen levels of a liquid culture comprising a nutrient media and such microorganism populations may be monitored to maintain or confirm a desired aerobic, microaerobic or anaerobic condition.

Conversion of 3HP to Acrylic Acid

The 3HP made by the process of this invention is converted to acrylic acid through dehydration. The conditions for this reaction are well known in the art, and the reaction typically produces AA and water. The water and other impurities are separated from AA by any conventional means, e.g., distillation or crystallization, in one or more steps. Following dehydration AOPA, a dimer of acrylic acid, may form. In one embodiment, a stream from the purification process, which stream contains AA and AOPA, and possibly unreacted 3HP, is recycled back to the dehydration reactor in which the AOPA is cracked back to AA. Recycling this stream also allows recovery of AA from a potential waste stream. As noted previously, the addition of AOPA and AA-containing recycle stream will not change the operating conditions or equipment. This recycle stream does not contain ammonia and as such, it will not affect the ABS/AS ratio.

Polymerization of Acrylic Acid

Acrylic acid obtained from the methods described in this disclosure may be further converted to various polymers. For example, the free-radical polymerization of acrylic acid takes place by polymerization methods known to the skilled worker and can be carried out, for example, in an emulsion or suspension in aqueous solution or another solvent. Initiators, such as but not limited to organic peroxides, are often added to aid in the polymerization. Among the classes of organic peroxides that may be used as initiators are diacyls, peroxydicarbonates, monoperoxycarbonates, peroxyketals, peroxyesters, dialkyls, and hydroperoxides. Another class of initiators is azo initiators, which may be used for acrylate polymerization as well as copolymerization with other monomers. U.S. Pat. Nos. 5,470,928; 5,510,307; 6,709,919; and 7,678,869 teach various approaches to polymerization using a number of initiators, including organic peroxides, azo compounds, and other chemical types, and are incorporated by reference for such teachings as applicable to the polymers described herein.

SPECIFIC EMBODIMENTS OF THE INVENTION

The following examples are given to illustrate the invention and should not be construed as limiting its scope. Example results are reported in the Table.

EXAMPLE 1

ABS Catalyzed Dehydration of Bio3HP at 1-Liter Scale

Bio-3HP broth produced by fermentation using a genetically-engineered strain of *E. coli* is centrifuged to remove cells and is concentrated on a rotary evaporator to produce a clarified aqueous concentrate containing 30 wt % 3HP. The clarified concentrate is diluted and the pH is adjusted to pH 2 with concentrated sulfuric acid, resulting in a dehydration feed concentration of 10.6 wt % 3HP. At pH 2, any ammonium ion present in the initial concentrate is converted to ABS.

A one-liter (1 L) glass reactor equipped with an electric heating mantle is charged with 300 grams (g) solid ABS (obtained from Sigma Aldrich, catalog number 09848) and 50 g of deionized (DI) water. The ABS solution is heated to 160° C. and overhead stirring is maintained to keep the solution uniform during heat-up and throughout the reaction. The bio-3HP feed is pumped at 1 milliliter per minute (mL/min) by a Watson Marlow 32 revolutions per minute (rpm) peristaltic pump operating at a 1% power setting onto or below the surface of the agitated liquid ABS catalyst. After completion of 3HP feeding and a hold period of 120 minutes, 50 mL of DI water is fed to the reactor at a rate of 1 mL/min. At a feed volume of 100 mL, just over 10 g of 3HP are fed during the run. Just over 8 g of acrylic acid are produced, resulting in a molar yield of 94%. High pressure liquid chromatography (HPLC) analysis is used for quantification of 3HP and acrylic acid in the feed and products.

EXAMPLES 2A AND 2B

Effect of Temperature on ABS-Catalyzed Dehydration of Bio3HP at 1-L Scale

Bio-3HP fermented by a genetically-engineered strain of *E. coli* is centrifuged to remove cells and is concentrated on a rotary evaporator to produce a clarified aqueous concentrate. The feed for both experiments are adjusted to pH 2 with concentrated sulfuric acid and had a final concentration of 22 wt % 3HP. A 1 L glass reactor equipped with an electric heating mantle is charged with 300 g solid ammonium bisulfate and 50 g of DI water. An ABS solution is heated to 165° C. and 180° C. for each of Examples 2A and 2B and overhead stirring is maintained to keep the solutions uniform during heating and throughout the reaction. The bio-3HP concentrate is pumped at 1 mL/min by a Watson-Marlow 32 rpm peristaltic pump operating at 1% power setting onto the surface of the agitated liquid ABS catalyst. After completion of 3HP feeding, 100 mL of DI water is similarly fed to the reactor at a rate of 1 mL/min. At a feed volume of 120 mL, just over 26 g of 3HP are fed to the reactor in each of the two experiments. Just under 20 g of acrylic acid are produced, resulting in a molar yield of 93% in both experiments showing that the reaction is not sensitive to temperature in the range of 165-180° C. HPLC analysis is used for quantification of 3HP and acrylic acid in the feed and products.

EXAMPLE 3

ABS-Catalyzed Dehydration of AOPA

AOPA feed is generated from an acrylic acid distillation column bottoms sample. This sample contains primarily AOPA with residual AA, and is diluted to approximately 15% sample in water. The feed to the dehydration reactor consists of 6.1% AA and 9.3% AOPA, the remaining 84.6% is deionized (DI) water. A one-liter glass reactor equipped with an electric heating mantle is charged with 300 grams (g) of solid ammonium bisulfate (obtained from Sigma Aldrich, catalog number 09848) and 50 g of DI water. The ABS solution is heated to 165° C. and overhead stirring is maintained to keep the solution uniform during heating and throughout the reaction. The diluted AOPA is pumped at one milliliter per minute (1 mL/min) by a Watson-Marlow 32 revolutions per minute (rpm) peristaltic pump operating at a 1% power setting onto the surface of the agitated liquid ABS catalyst. After completion of 3HP feeding, 100 mL of DI water is similarly fed to the reactor at a rate of 1 mL/min. At a feed volume of 100 mL, 26.8 g of 3HP equivalents are fed to the reactor in each of the two runs. 3HP equivalents are a theoretical value used for calculation purposes when a compound related to, but distinct from, 3HP is fed to the reactor. In this case, AA and AOPA are both mathematically converted on a molar basis to generate the equivalent mass of 3HP. 20.8 g of acrylic acid are recovered or produced, depending on whether the parent molecule is fed as AA or as AOPA. This results in a molar yield/recovery of 97% demonstrating that distillation column bottoms containing AOPA can be fed under 3HP dehydration conditions to recover the yield loss that occurs when AOPA forms. HPLC analysis is used for quantification of 3HP and acrylic acid in the feed and products.

TABLE

Results of Examples 1-3

| | | g AA collected | | | | | | | | Molar AA Yield (%) | | |
|---|---|---|---|---|---|---|---|---|---|---|---|---|
| | g 3HP fed (Ex 1-2) | 1st hr | 2nd hr | 3rd hr | 4th hr | 5th hr | Total | During Feed (approx) | During Water Wash (approx) | Total | During 3HP Feed (approx) | During Wash (approx) |
| Example 1 | 10.5 | 0.07 | 4.7 | 1.4 | 0.19 | 1.8 | 8.16 | 4.77 | 3.39 | 97.1% | 56.7% | 40.4% |
| Example 2A | 26.1 | 3 | 8.7 | 6.9 | 1.2 | 0 | 19.8 | 11.7 | 8.10 | 94.8% | 56% | 38.8% |
| Example 2B | 26.3 | 4.7 | 10.4 | 4.7 | 0.31 | 0 | 20.13 | 15.09 | 5.04 | 95.8% | 71.9% | 23.8% |
| Example 3 | 26.8* | 9.9 | 9.2 | 1.7 | 0 | 0 | 20.8 | 19.1 | 1.7 | 97.0% | 89.1% | 7.9% |

What is claimed is:

1. A process comprising the steps of:
   (A) Contacting in a reaction zone and under dehydration reaction conditions a beta-hydroxy carboxylic acid and/or its ammonium salt with a catalytic amount of a catalyst comprising ammonium bisulfate (ABS) to form a dehydrated carboxylic acid, water and ammonium sulfate (AS),
   (B) Removing a vapor stream comprising the dehydrated carboxylic acid and water from the reaction zone,
   (C) Removing a liquid stream comprising AS from the reaction zone,
   (D) Forwarding the vapor stream to a purification zone in which the dehydrated carboxylic acid is separated from water,
   (E) Forwarding the liquid stream comprising AS to a thermal conversion zone in which the AS is converted to ABS and ammonia,
   (F) Optionally, recycling the ABS from step (E) to step (A),
   (G) Optionally, recovering ammonia from the thermal conversion zone, and
   (H) Optionally, removing a purge stream comprising ABS and/or AS prior to or at or near the beginning of the thermal conversion zone.

2. The process of claim 1 wherein steps A-C are operated in a continuous manner.

3. The process of claim 1 in which the beta-hydroxy carboxylic acid and/or its ammonium salt are 3-hydroxypropionic acid and/or its ammonium salt.

4. The process of claim 1 in which the dehydration reaction conditions include a temperature of 100° C. to 250° C. and a pressure of 26.6 kiloPascals (KPa) to 101.3 KPa.

5. The process of claim 1 comprising the additional step (F) of recycling the ABS from step (E) to step (A).

6. The process of claim 5 comprising the additional step (G) of recovering ammonia from the thermal conversion zone.

7. The process of claim 6 comprising the additional step (H) of removing a purge stream comprising ABS and/or AS prior to or at or near the beginning of the thermal conversion zone.

8. The process of claim 1 in which acryloxypropionic acid (AOPA) is produced in the purification zone.

9. The process of claim 8 comprising the additional step of recycling a stream comprising AOPA from the purification zone to the reaction zone.

10. The process of claim 9 wherein the recycle stream further comprises the dehydrated carboxylic acid.

11. The process of claim 1 wherein the dehydrated carboxylic acid is acrylic acid.

12. The process of claim 1 wherein step A comprises contacting in the reaction zone and under dehydration reaction conditions (i) the beta-hydroxy carboxylic acid and (ii) 60 wt % of its ammonium salt, based on the combined amount of beta-hydroxy carboxylic acid and its ammonium salt, with (iii) a catalytic amount of the catalyst comprising ammonium bisulfate (ABS).

* * * * *